US005294543A

United States Patent [19]

Lerner et al.

[11] Patent Number: 5,294,543

[45] Date of Patent: Mar. 15, 1994

[54] INHIBITOR OF PLATELET AGGREGATION

[75] Inventors: Ethan A. Lerner, Brookline, Mass.; Michael R. Lerner, Hamden, Conn.

[73] Assignee: The General Hospital Corporation, Boston, Mass.

[21] Appl. No.: 865,166

[22] Filed: Apr. 8, 1992

[51] Int. Cl.[5] ........................ C12N 15/11; C12N 15/63; C07K 7/10; C07K 15/12

[52] U.S. Cl. ................................ 435/69.1; 435/172.3; 435/320.1; 435/252.3; 435/240.2; 536/23.1; 530/350; 514/12; 514/822; 514/824; 935/11; 935/23; 935/24; 935/56; 935/66

[58] Field of Search ................. 435/69.1, 172.3, 320.1, 435/252.3, 240.2; 536/27, 23.1; 935/11, 23, 24, 66, 56

[56] References Cited

FOREIGN PATENT DOCUMENTS

PCT/US90/-03746 6/1990 PCT Int'l Appl. .

OTHER PUBLICATIONS

Ribeiro, Annual Review of Entomology, 1987, vol. 32, pp. 463-478.

Ribeiro et al., Insect Biochem, 1989, vol. 19 No. 4, pp. 409-412.

Lerner et al., The Journal of Biological Chemistry, Jun. 13, 1991, vol. 266 No. 17, pp. 11234-11236.

Ribeiro et al., Comp. Biochem. Physiol., 1991, vol. 100A No. 1, pp. 109-112.

Ribeiro et al., Science, Jan. 1989, vol. 243, pp. 212-214.

James et al., Parasitol. Today, Oct. 1991, vol. 7, pp. 267-271.

Gould et al., Proc. Soc. Exp. Biol. Med., 1990, pp. 168-171.

Bang, Circulation, Jul. 1991, vol. 84 No. 1, pp. 436-438.

Lerner, Clinical Research, 1991, vol. 39 No. 2.

Musial et al., Circulation, Jul. 1990, vol. 82 No. 1, pp. 261-273.

*Primary Examiner*—Robert A. Wax

*Assistant Examiner*—Rebecca Prouty

*Attorney, Agent, or Firm*—Lahive & Cockfield

[57] ABSTRACT

Purified DNA comprising a sequence encoding chrysoptin.

Chrysoptin can be used to alter the hemodynamic or hemostatic properties of an animal's blood by administering to the animal an effective amount of chrysoptin.

28 Claims, No Drawings

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 30
( B ) TYPE: amino acid
( C ) STRANDEDNESS:
( D ) TOPOLOGY: linear ( x i ) SEQUENCE DESCRIPTION: SEQ ID NO: 1:

```
Val Ser Tyr Cys Ser Leu Pro Cys Arg Gly Asp Ser His Val Gly Cys
 1               5                  10                  15

Gly Glu Ala Ala Tyr Gly Val Glu Cys Gly Gln Ser Pro Arg
            20                  25                  30
```

( 2 ) INFORMATION FOR SEQ ID NO: 2:

( i ) SEQUENCE CHARACTERISTICS:
( A ) LENGTH: 18
( B ) TYPE: amino acid
( C ) STRANDEDNESS:
( D ) TOPOLOGY: linear ( x i ) SEQUENCE DESCRIPTION: SEQ ID NO: 2:

Phe Trp Leu Pro Gly Gln Leu Asn Phe Glu Tyr Thr Gly Asp Lys Leu
 1           5                       10                    15

Pro Arg ( 2 ) INFORMATION FOR SEQ ID NO: 3:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 3:

Ala Leu Leu Thr Cys Asn Phe Ser Ser Asp Asn Ile Tyr Gly Arg Pro
 1           5                       10                    15

Val Tyr Lys ( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GCCCTSCTSA CYTGYAAYTT                                                      20

( 2 ) INFORMATION FOR SEQ ID NO: 5:

( i ) SEQUENCE CHARACTERISTICS:
        ( A ) LENGTH: 203
        ( B ) TYPE: nucleic acid
        ( C ) STRANDEDNESS: double
        ( D ) TOPOLOGY: linear ( x i ) SEQUENCE DESCRIPTION: SEQ ID NO: 5:

ACT TGC AAC TTT TCT TCG GAT AAT GAC TAT AAC CGT CCT GTA TAC AAG      48
Thr Cys Asn Phe Ser Ser Asp Asn Asp Tyr Asn Arg Pro Val Tyr Lys
 1           5                       10                    15

ACC GGT AGC AGT CCT GCA GAA AAA TGT ATA AAA AAA GAC AAA ACA TTC      96
Thr Gly Ser Ser Pro Ala Glu Lys Cys Ile Lys Lys Asp Lys Thr Phe
            20                      25                  30

AAA AAT TTA TGT TCC GCT GAG GAG CCT ATT GAT CCA AAC CAA CAT AAT     144
Lys Asn Leu Cys Ser Ala Glu Glu Pro Ile Asp Pro Asn Gln His Asn
        35                   40                      45

TTC TAATCAGCAT TGAGCTTGAA AATGAGTAAA TAAACTTATA TATCGCAAAA AAAAAA   203
Phe ( 2 ) INFORMATION FOR SEQ ID NO: 6:

( i ) SEQUENCE CHARACTERISTICS:
        ( A ) LENGTH: 49
        ( B ) TYPE: amino acid
        ( C ) STRANDEDNESS:
        ( D ) TOPOLOGY: linear ( x i ) SEQUENCE DESCRIPTION: SEQ ID NO: 6:

Thr Cys Asn Phe Ser Ser Asp Asn Asp Tyr Asn Arg Pro Val Tyr Lys
 1           5                       10                    15

Thr Gly Ser Ser Pro Ala Glu Lys Cys Ile Lys Lys Asp Lys Thr Phe
            20                      25                  30

Lys Asn Leu Cys Ser Ala Glu Glu Pro Ile Asp Pro Asn Gln His Asn
        35                   40                      45

-continued

Phe

INHIBITOR OF PLATELET AGGREGATION

BACKGROUND OF THE INVENTION

Bioactive substances in the saliva of hematophagous arthropods facilitate blood feeding by preventing hemostasis or by altering local hemodynamics.

SUMMARY OF THE INVENTION

In general, the invention features, purified DNA including a sequence encoding chrysoptin.

The invention also features a vector comprising a DNA sequence encoding chrysoptin. Preferred embodiments include: a cell containing purified DNA including a sequence encoding chrysoptin and preferably capable of expressing chrysoptin; an essentially homogeneous population of cells, each of which includes purified DNA including a sequence encoding chrysoptin DNA; and chrysoptin produced by expression of the purified DNA.

In another aspect, the invention features, a purified preparation of chrysoptin.

In another aspect, the invention features, a therapeutic composition including chrysoptin and a pharmaceutically acceptable carrier.

In another aspect, the invention features, a method for manufacture of chrysoptin including culturing a cell containing purified DNA including a sequence encoding chrysoptin in a medium to express the chrysoptin.

In another aspect, the invention features, a method for altering the hemodynamic or the hemostatic properties of an animal's, e.g., a human's, blood including administering to the animal an effective amount of purified chrysoptin.

In another aspect, the invention features, a method for treating an animal, e.g., a human, having or at risk for having a cardiovascular disorder including: identifying an animal having or at risk for having the cardiovascular disorder; and administering a therapeutically-effective amount of chrysoptin to the animal.

In another aspect, the invention features, a method for treating an animal, e.g., a human, having a disorder characterized by unwanted blood clotting including: identifying an animal having a disorder characterized by unwanted blood clotting; and administering a therapeutically-effective amount of chrysoptin to the animal.

In another aspect, the invention features, a method for inhibiting the blockage of an artery including; identifying an animal, e.g., a human, at risk for a blocked artery, e.g., a coronary artery; and administering a therapeutically-effective amount of chrysoptin to the animal.

In another aspect, the invention features, a method of preventing a cardiovascular disorder, e.g., a heart attack, in an animal, e.g., a human, including; identifying an animal at risk for the disorder; and administering to the animal an effective amount of chrysoptin.

Purified DNA is DNA that is not immediately contiguous with both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced e.g., by PCR (polymerase chain reaction) or restriction endonuclease treatment) independent of other DNA sequences. It also includes a recombinant DNA which is part of a hybrid gene encoding an additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, if 6 of 10 of the positions in two sequences are matched or homologous then the two sequences are 60% homologous. By way of example, the DNA sequences ATTGCC and TATGGC share 50% homology.

A purified preparation of a chrysoptin polypeptide is a preparation which is purer than the saliva of the organism in which the chrysoptin naturally occurs.

The methods and compounds of the invention are useful for: studying the mechanisms of platelet function and hemostasis; treating patients having a cardiovascular diseases, e.g., heart disease or a disease characterized by unwanted blood clotting; and as an antagonist of the fibrinogen receptor.

Other features and advantages of the invention will be apparent from the following description and from the claims.

DETAILED DESCRIPTION

Isolation of chrysoptin

Because the painful bites from deerflies, better known as "greenheads" sometimes ooze blood, salivary gland extracts from these flies (genus Chrysops) were examined to test the effect of such extracts on platelet aggregation. Inhibitors of platelet aggregation have not previously been isolated from these insects but anti-platelet activity has been found in a number of viper venoms and they all contain the integrin binding sequence Arg-Gly-Asp- (RGD). These proteins act by binding to the fibrinogen receptor on platelets.

Deerflies were collected and salivary glands dissected under a microscope, and placed in ice-cold phosphate buffered saline. The glands were stored at −70° C. until use. To prepare extracts, the glands were thawed, vortexed, refrozen on dry ice, thawed again, and vortexed. Before running on HPLC, the extracts were spun in a microcentrifuge at 10,000 rpm for 1 minute to remove debris. They were then mixed with an equal volume of buffer A (50 mM $NaH_2PO_4$/2.0M $NH_4OS_4$ at pH 7.4) and 30 microliters injected onto a SMART system HPLC (Pharmacia) which had a phenyl superose "precision column 1.6/5" hydrophobic interaction column. Flow was at 50 microliters per minute and the gradient went from 100% buffer A to 100% buffer B (50 mM $NaH_2PO_4$, pH 7.4 over 30 minutes beginning 12 minutes after injection. The active peak eluted at 33.41 minutes when the salt concentrations was 0.506M ammonium sulfate. Detection was at 214 nm.

The peak isolated from HPLC was desalted and concentrated with a Centricom-30 device prior to testing for activity. Fractions were assayed for inhibition of platelet aggregation by standard nephelometric techniques (see, e.g., Born and Cross. The aggregation of blood platelets. J. Physiol. 1963. 168:178–195, hereby incorporated by reference) in which venous blood was obtained from volunteers who had not ingested caffeine-containing beverages for at least 12 hours or acetylsalicylic acid for at least 10 days. The blood was anticoagulated with 13 mM sodium citrate and used within one hour. Platelet-rich plasma was prepared by centrifugation at 160 g for 10 minutes at 22° C. Aggregations were monitored in a Platelet Aggregation Profiler Model PAP-4 (Bio/Data Corporation) in which 0.2 ml aliquots of platelet-rich plasma were incubated at 37° C. and stirred at 1000 rpm. Agonists used to induce aggregation included 5 μM ADP, 0.05 U thrombin, or 10 μM calcium ionophore A-23187. Fractions of deerfly extract were added to aliquots of platelet-rich plasma one minute prior to addition of agonist.

The active peak was subjected to SDS-PAGE electrophoresis and ran with MW of approximately 20,000 d.

Biological activity of chrysoptin

Using the standard nephelometric techniques described above, chrysoptin was found to completely and dose-dependently inhibit (with an $IC_{50}$ of 16nM) platelet aggregation induced by 5 μM ADP. In addition, chrysoptin completely inhibited platelet aggregation induced by either 0.05 U thrombin or 1O μM calcium ionophore A-23187.

Preliminary studies have not demonstrated an effect of deerfly salivary gland extracts on cGMP or cAMP levels. In one experiment, salivary gland extracts competed with labeled fibrinogen on washed platelets. Thus, chrysoptin appears to bind to the fibrinogen receptor.

Amino acid sequence analysis of chrysoptin

Chrysoptin used for amino acid sequencing was purified as described above. The chrysoptin-containing hydrophobic interaction column-fraction was further dialyzed against water and then applied to an Applied Biosystems 477a pulsed liquid sequencer for determination of the N-terminal amino acid sequence. The N-terminal sequence of chrysoptin is Val-Ser-Tyr-Cys-Ser-Leu-Pro-Cys-Arg-Gly-Asp-Ser-His-Val-Gly-Cys-Gly-Glu-Ala-Ala-Tyr-Gly-Val-Glu-Cys-Gly-Gln-Ser-Pro-Arg (Seq. ID No. 1). Note that chrysoptin has an Arg-Gly-Asp (RGD) motif at position 10–12. This motif has been found in snake viper venoms and is thought to be important to binding to the fibrinogen receptor. Synthetic RGD peptides bind this and other integrin receptors.

A chrysoptin-containing hydrophobic interaction column-fraction was also digested with trypsin and the resulting fragments separated and collected by reverse-phase HPLC. The larger two fractions collected from this HPLC run were also sequenced and gave the following sequences: Phe-Trp-Leu-Pro-Gly-Gln-Leu-Asn-Phe-Glu-Tyr-Thr-Gly-Asp-Lys-Leu-Pro-Arg (Seq. ID No. 2) and Ala-Leu-Leu-Thr-Cys-Asn-Phe-Ser-Ser-Asp-Asn-Ile-Tyr-Gly-Arg-Pro-Val-Tyr-Lys (Seq. ID No. 3).

Cloning chrysoptin

Degenerate oligonucleotides corresponding to various regions of the above-described tryptic fragment sequences and to the N-terminal sequences were made and an oligo corresponding to the first 6 amino acids (GCC-CTG/C-CTG/C-ACC/T-TGC/T-AAC/T-TT (Seq. ID No. 4)) of this last amino acid sequence (Seq ID No. 3) was used in a polymerase chain reaction with oligo-dT to amplify cDNA made from deerfly salivary gland RNA. An approximately 300 bp band was found. The amplified band was subcloned and sequenced using standard techniques. Its sequence is: ACTT-GCAACTTTTCTTCGGATAATGAC-TATAACCGTCCTGTATACAAGACCGGTAG-CAGT CCTGCAGAAAAATG-TATAAAAAAAGACAAAACATTCAAAAATT-TATGTTCCGCTGAGGAG CCTATTGATC-CAAACCAACATAATTTCTAATCAGCATT-GAGCTTGAAAATGAGTAAATAA AGT-TATATATCGCAAAAAAAAAA (Seq. ID No. 5)

This corresponds to the predicted C-terminal amino acid sequence of chrysoptin which is: Thr Cys Asn Phe Ser Ser Asp Asn Asp Tyr Asn Arg Pro Val Tyr Lys Thr Gly Ser Ser Pro Ala Glu Lys Cys Ile Lys Lys Asp Lys Thr Phe Lys Asn Leu Cys Ser Ala Glu Glu Pro Ile Asp Pro Asn Gln His Asn Phe (Seq. ID No. 6). This sequence aligns well with the information obtained from amino acid sequencing (Seq. ID No. 3) except that isoleucine at position 12 (of Seq. ID No. 3) is predicted to be an Asp by the cDNA sequence and likewise, the Glycine at position 14 (of Seq. ID No. 3) is predicted to be an Asn. Note however, that codon usage and bias are unknown in deerflies.

The sequence data provided above can be used to obtain the remainder of the chrysoptin sequence by the routine application of standard methods known to those skilled in the art. For example, the 5' end of the cDNA can be obtained using a RACE reaction (rapid amplification of cDNA ends) involving cDNA synthesis using a non-degenerate oligonucleotide and reverse transcriptase combined with homopolymeric tailing of the 5'end of the cDNA and subsequent amplification of the cDNA. Once a complete cDNA is available standard methods known to those skilled in the art can be used to obtain the genomic sequence, make sequence comparisons with other genes and other genomes, and to express the gene in a suitable expression system, e.g. baculovirus.

Use

Substances of the invention can be administered to alter the hemostatic or hemodynamic properties of the blood, e.g., to provide internal fibrolytic therapy to prevent coronary artery blockage. Dosages of the substances of the invention will vary, depending on factors such as the half-life of the substance, the potency of the substance, the route of administration, and the condition of the patient. Generally, chrysoptin should be administered to the patient in such a way that it is present in the blood stream. The peptides of the invention may be administered to a mammal, particularly a human, in one of the traditional modes e.g., intravenously, orally, parenterally, transdermally, intravenously, or transmucosally, or by expression of chrysoptin encoding nucleic acid in the patient, e.g., in transformed endothelial cells.

Other Embodiments

The invention includes any protein which is substantially homologous to chrysoptin from the fly Chrysops as well as other naturally occurring arthropod chrysoptins. Also included are: allelic variations; natural mutants; induced mutants; proteins encoded by DNA that hybridizes under high or low stringency conditions to a naturally occurring nucleic acid (for definitions of high and low stringency see Current Protocols in Molecular Biology, John Wiley & Sons, New York, 1989, 6.3.1–6.3.6, hereby incorporated by reference); and polypeptides or proteins specifically bound by antisera to chrysoptin, especially by antisera to the active site or binding domain of chrysoptin. The term also includes chimeric polypeptides that include chrysoptin.

The invention also includes analogs of naturally occurring chrysoptin polypeptides. Analogs can differ from naturally occurring chrysoptin by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring chrysoptin sequence. The length of comparison sequences will generally be at least about 8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring chrysoptin by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), *Molecular Cloning: A Laboratory Manual* (2d ed.), CSH Press, hereby incorporated by reference. Also included are analogs that include residues other than naturally occurring L-amino acids, e.g., D-amino acids or non-naturally occurring or synthetic amino acids, e.g., $\beta$ or $\gamma$ amino acids.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of chrysoptin can be generated by methods known to those skilled in the art. The ability of a candidate fragment to exhibit a biological activity of chrysoptin can be assessed by methods described herein and by those known to those skilled in the art. Also included are chrysoptin polypeptides containing amino acids that are normally removed during protein processing, including additional amino acids that are not required for the biological activity of the polypeptide, or including additional amino acids that result from alternative mRNA splicing or alternative protein processing events.

A chrysoptin polypeptide, fragment, or analog is biologically active if it exhibits a biological activity of a naturally occurring chrysoptin, e.g., the ability to inhibit platelet aggregation (as measured in the assay described above) at least 10% as effectively as does native chrysoptin. (To be at least 10% as effective as native chrysoptin means a sample of the polypeptide, fragment, or analog must have the ability to provide at least the same level of inhibition as does a sample of native chrysoptin of 1/10 its weight).

Other embodiments are within the following claims.

What is claimed is:

1. Purified DNA comprising a sequence that hybridizes under high stringency to a naturally occurring Chrysops nucleic acid encoding the amino acid sequence of Val-Ser-Tyr-Cys-Ser-Leu-Pro-Cys-Arg-Gly-Asp-Ser-His-Val-Gly-Cys-Gly-Glu-Ala-Ala-Tyr-Gly-Val-Glu-Cys-Gly-Gln-Ser-Pro-Arg (Seq. ID No. 1), the amino acid sequence Phe-Trp-Leu-Pro-Gly-Gln-Leu-Asn-Phe-Glu-Tyr-Thr-Gly-Asp-Lys-Leu-Pro-Arg (Seq. ID No. 2), the amino acid sequence Ala-Leu-Leu-Thr-Cys-Asn-Phe-Ser-Ser-Asp-Asn-Ile-Tyr-Gly-Arg-Pro-Val-Tyr-Lys (Seq. ID No. 3), or the amino acid sequence Thr-Cys-Asn-Phe-Ser-Ser-Asp-Asn-Asp-Tyr-Asn-Arg-Pro-Val-Try-Lys-Thr-Gly-Ser-Ser-Pro-Ala-Glu-Lys-Cys-Ile-Lys-Lys- Asp-Lys-Thr-Phe-Lys-Asn-Leu-Cys-Ser-Ala-Glu-Glu-Pro-Ile-Asp-Pro-Asn-Gln-His-Asn-Phe (Seq. ID No. 6).

2. A vector comprising the purified DNA of claim 1.

3. A cell containing the purified DNA of claim 1.

4. The cell of claim 3, wherein said cell is capable of expressing chrysoptin.

5. An essentially homogeneous population of cells, each of which comprises the isolated DNA of claim 1.

6. A method for manufacture of chrysoptin comprising culturing the cell of claim 3 in a medium to express said chrysoptin.

7. The purified DNA of claim 1, wherein said DNA encodes a peptide at least 20 amino acids in length.

8. The purified DNA of claim 1, wherein said DNA encodes a peptide at least 30 amino acids in length.

9. The purified DNA of claim 1, wherein said DNA encodes a peptide at least 40 amino acids in length.

10. The purified DNA of claim 1, wherein said DNA encodes a peptide at least 50 amino acids in length.

11. The purified DNA of claim 1, wherein said DNA encodes a peptide at least 60 amino acids in length.

12. The purified DNA of claim 1, wherein said DNA encodes a peptide at least 80 amino acids in length.

13. Purified DNA comprising a sequence which encodes a peptide which is at least 90 percent homologous with the amino acid sequence of Val-Ser-Tyr-Cys-Ser-Leu-Pro-Cys-Arg-Gly-Asp-Ser-His-Val-Gly-Cys-Gly-Glu-Ala-Ala-Tyr-Gly-Val-Glu-Cys-Gly-Gln-Ser-Pro-Arg (Seq. ID No. 1), the amino acid sequence Phe-Trp-Leu-Pro-Gly-Gln-Leu-Asn-Phe-Glu-Tyr-Thr-Gly-Asp-Lys-Leu-Pro-Arg (Seq. ID No. 2), the amino acid sequence Ala-Leu-Leu-Thr-Cys-Asn-Phe-Ser-Ser-Asp-Asn-Ile-Tyr-Gly-Arg-Pro-Val-Tyr-Lys (Seq. ID No. 3), or the amino acid sequence Thr-Cys-Asn-Phe-Ser-Ser-Asp-Asn-Asp-Tyr-Asn-Arg-Pro-Val-Try-Lys-Thr-Gly-Ser-Ser-Pro-Ala-Glu-Lys-Cys-Ile-Lys-Lys-Asp-Lys-Thr-Phe-Lys-Asn-Leu-Cys -Ser-Ala-Glu-Glu-Pro-Ile-Asp-Pro-Asn-Gln-His-Asn-Phe (Seq. ID No. 6), said peptide having the ability of inhibit platelet aggregation at least 10% as effectively as does native chrysoptin.

14. The purified DNA of claim 13, wherein said homology is at least 95%.

15. The purified DNA of claim 13, wherein said encoded peptide is at least 20 amino acids in length.

16. The purified DNA of claim 13, wherein said encoded peptide is at least 30 amino acids in length.

17. The purified DNA of claim 13, wherein said encoded peptide is at least 40 amino acids in length.

18. The purified DNA of claim 13, wherein said encoded peptide is at least 50 amino acids in length.

19. The purified DNA of claim 13, wherein said encoded peptide is at least 60 amino acids in length.

20. The purified DNA of claim 13, wherein said encoded peptide is at least 80 amino acids in length.

21. Purified DNA comprising a sequence which encodes the amino acid sequence of Val-Ser-Tyr-Cys-Ser-Leu-Pro-Cys-Arg-Gly-Asp-Ser-His-Val-Gly-Cys-Gly-Glu-Ala-Ala-Tyr-Gly-Val-Glu-Cys-Gly-Gln-Ser-Pro-Arg (Seq. ID No. 1), the amino acid sequence Phe-Trp-Leu-Pro-Gly-Gln-Leu-Asn-Phe-Glu-Tyr-Thr-Gly-Asp-Lys-Leu-Pro-Arg (Seq ID No. 2), the amino acid sequence Ala-Leu-Leu-Thr-Cys-Asn-Phe-Ser-Ser-Asp-Asn-Ile-Tyr-Gly-Arg-Pro-Val-Tyr-Lys (Seq. ID No. 3), or the amino acid sequence Thr-Cys-Asn-Phe-Ser-Ser-Asp-Asn-Asp-Tyr-Asn-Arg-Pro-Val-Try-Lys-Thr-Gly-Ser-Ser-Pro-Ala-Glu-Lys-Cys-Ile-Lys-Lys-Asp-Lys-Thr-Phe-Lys-Asn-Leu-Cys -Ser-Ala-Glu-Glu-Pro-Ile-Asp-Pro-Asn-Gln-His-Asn-Phe (Seq. ID No. 6).

22. The purified DNA of claim 21, wherein said DNA encodes a peptide which has the ability to inhibit platelet aggregation at least 10% as effectively as does native chrysoptin.

23. The purified DNA of claim 21, wherein said DNA encodes a peptide at least 20 amino acids in length.

24. The purified DNA of claim 21, wherein said DNA encodes a peptide at least 30 amino acids in length.

25. The purified DNA of claim 21, wherein said DNA encodes a peptide at least 40 amino acids in length.

26. The purified DNA of claim 21, wherein said DNA encodes a peptide at least 50 amino acids in length.

27. The purified DNA of claim 21, wherein said DNA encodes a peptide at least 60 amino acids in length.

28. The purified DNA of claim 21, wherein said DNA encodes a peptide at least 80 amino acids in length.

* * * * *